(12) United States Patent
Deming et al.

(10) Patent No.: US 9,718,921 B2
(45) Date of Patent: Aug. 1, 2017

(54) AMPHIPHILIC DERIVATIVES OF THIOETHER CONTAINING BLOCK COPOLYPEPTIDES

(71) Applicant: The Regents of the University of California, Oakland, CA (US)

(72) Inventors: Timothy J. Deming, Los Angeles, CA (US); Jessica R. Kramer, Oakland, CA (US); April R. Rodriguez, Marina Del Rey, CA (US)

(73) Assignee: The Regents of the University of California, Oakland, CA (US)

( * ) Notice: Subject to any disclaimer, the term of this patent is extended or adjusted under 35 U.S.C. 154(b) by 23 days.

(21) Appl. No.: 14/770,417

(22) PCT Filed: Feb. 26, 2014

(86) PCT No.: PCT/US2014/018763
§ 371 (c)(1),
(2) Date: Aug. 25, 2015

(87) PCT Pub. No.: WO2014/134203
PCT Pub. Date: Sep. 4, 2014

(65) Prior Publication Data
US 2016/0002405 A1  Jan. 7, 2016

Related U.S. Application Data

(60) Provisional application No. 61/769,702, filed on Feb. 26, 2013.

(51) Int. Cl.
| | |
|---|---|
| *C08G 69/48* | (2006.01) |
| *A61K 47/42* | (2017.01) |
| *C08G 69/10* | (2006.01) |
| *C08G 69/42* | (2006.01) |
| *A61K 47/34* | (2017.01) |
| *A61K 9/127* | (2006.01) |

(52) U.S. Cl.
CPC ............ *C08G 69/48* (2013.01); *A61K 9/1273* (2013.01); *A61K 47/34* (2013.01); *A61K 47/42* (2013.01); *C08G 69/10* (2013.01); *C08G 69/42* (2013.01)

(58) Field of Classification Search
None
See application file for complete search history.

(56) References Cited

U.S. PATENT DOCUMENTS

| | | | |
|---|---|---|---|
| 4,165,332 | A | 8/1979 | Beard et al. |
| 7,132,475 | B2 | 11/2006 | Hubbell et al. |
| 2010/0222407 | A1 | 9/2010 | Segura et al. |
| 2011/0177508 | A1 | 7/2011 | Bestor et al. |
| 2011/0223217 | A1 | 9/2011 | Dixon et al. |
| 2014/0294932 | A1 | 10/2014 | Kim et al. |

FOREIGN PATENT DOCUMENTS

| | | |
|---|---|---|
| EP | 0226827 A2 | 7/1987 |
| WO | WO-2010/023670 A2 | 3/2010 |
| WO | WO-2013-148727 A1 | 10/2013 |

OTHER PUBLICATIONS

Alferiev, Ivan S., et al. "High reactivity of alkyl sulfides towards epoxides under conditions of collagen fixation—a convenient approach to 2-amino-4-butyrolactones," Biomaterials, 22: 2501-06 (2001).
Gharakhanian, Eric G., et al. "Versatile Synthesis of Stable, Functional Polypeptides via Reaction with Epoxides," Biomacromolecules, 16: 1802-1806 (2015).
Kramer, Jessica R., et al. "Preparation of Multifunctional and Multireactive Polypeptides via Methionine Alkylation," Biomacromolecules, 13: 1719-23 (2012).
International Search Report from corresponding International Application No. PCT/US2016/023428, mailed Jun. 29, 2016.
Extended European Search Report issued by the European Patent Office, dated Jan. 28, 2016, in related Application No. EP 15306247.
Ribeiro et al., "Influence of the amino-acid sequence on the inverse temperature transition of elastin-like polymers," Biophys J, 97:312-20 (2009).
Teeuwen et al., "'Clickable' elastins: elastin-like polypeptides functionalized with azide or alkyne groups," Chem Comm, 4022-4 (2009).
Hanson et al., "Nonionic block copolypeptide micelles containing a hydrophobic rac-leucine core," Macromolecules, 43:6268-9 (2010).
Huang et al., "Biologically active polymersomes from amphiphilic glycopeptides," J Am Chem Soc, 134:119-22 (2011).
International Search Report from corresponding International Application No. PCT/US2014/018763, mailed Jun. 2, 2014.
Kramer et al., "Glycopolypeptide conformations in bioactive block copolymer assemblies influence their nanoscale morphology," Soft Matter, 9(12):3389-95 (2013).
Catalog page for 2 bromoethyl triflate from ABX, http://web.archive.org/web/20090706013707/http://abx.de/chemicals/6182.html, available online Jul. 2009.
International Search Report and Written Opinion for International Application No. PCT/US2013/033938 dated Jul. 22, 2013.
Kaplowitz, et al., "The importance and regulation of hepatic glutathione," Yale J Biol Med, 54: 497-502 (1981).
Kultyshev, et al., "S-Alkylation and S-Amination of Methyl Thioethers—Derivative of closo-[B12H12]2-. Synthesis of a Boronated Phosphonate, gem-Bisposphonates, and Dodecaborane-ortho-carborane Oligomers," J Am Chem Soc, 124(11): 2614-2624 (2002).

(Continued)

*Primary Examiner* — Ana Woodward
(74) *Attorney, Agent, or Firm* — Foley Hoag LLP (57) ABSTRACT

Methods for preparation of novel amphiphilic derivatives of thioether containing block copolypeptides with narrow chain length distributions are described. These block copolymers can be chemically modified by oxidation and alkylation of the thioether containing residues. These materials generate self-assembled micelles, vesicles and hydrogels, or emulsions with oil phases. These assemblies can be used to encapsulate and delivery therapeutic molecules. The assemblies can be taken up by cells to release molecules from the assemblies.

12 Claims, 5 Drawing Sheets

(56) References Cited

OTHER PUBLICATIONS

Kyte, et al., "Purification of peptides that contain methionine residues," Method Enzymol, 91: 367-377 (1983).
March, Jerry Advanced Organic Chemistry (1992) ISBN 0-471-60180-2, p. 294-298 and p. 352-354.
Pande, et al., "Suppression of phase separation in solutions of bovine lambda IV-crestallin by polar modification of the sulfur-containing amino acids," PNAS, 88(11): 4916-4920 (1991).
Reid, et al., "Selective identification and quantitative analysis of methionine containing peptides by charge derivatization and tandem mass spectrometry," J Am Soc Mass Spectr, 16(7): 1131-1150 (2005).
Stark, et al., "Alkylation of the methionine residues of ribonuclease in 8M urea," J Biol Chem, 269(11): 3755-3761 (1964).
Storer, et al., "Aracyl triflates for preparing fluorescent and UV absorbing derivatives of unreactive carboxylates, amines, and other reactive metabolites," Analytica Chimic Acta, 558: 319-325 (2006).
Supplementary European Search Report dated Sep. 16, 2016 from EP 14 75 7627.
Taichi, et al., "Suppression of side reactions during final deprotection employing a strong acid in boc chemistry: regeneration of methionyl residues from their sulfonium salts," Int J Peptide Res Ther, 15(4): 247-253 (2009).
Toennies, et al., "Methionine Studies VII. Sulfonium Derivatives," Journal of the American Chemical Society, vol. 67, 1945, pp. 849-851.
Umemura, et al., "Alkylation of several nucleophiles with alkylsulfonium salts," Bull Chem Soc Japan, 63: 2593-2600 (1990).

AMPHIPHILIC DERIVATIVES OF THIOETHER CONTAINING BLOCK COPOLYPEPTIDES

CROSS-REFERENCE TO PRIOR APPLICATIONS

This application is a U.S. National Phase of International Application No. PCT/US2014/018763, filed on 26 Feb. 2014, which claims priority to U.S. Provisional Patent Application No. 61/769,702 filed on 26 Feb. 2013, the entire contents of each are incorporated herein by reference.

U.S. GOVERNMENT SUPPORT

This invention was made with Government support under Grant Numbers DMR0907453, MSN1057970, awarded by the National Science Foundation. The Government has certain rights in the invention.

BACKGROUND OF THE INVENTION

Area of the Art
This invention is in the area of block copolypeptides and more specifically describes synthesis, properties and uses of thioether-containing block copolypeptides.

SUMMARY OF THE INVENTION

The present invention includes methods for preparation of novel amphiphilic derivatives of thioether containing block copolypeptides with narrow chain length distributions. These block copolymers can be chemically modified by oxidation and alkylation of thioether containing residues (e.g. methionine) to provide a variety of novel amphiphilic block copolymers. Methods to generate self-assembled micelles, vesicles and hydrogels, or emulsions with oil phases, from these amphiphilic block copolymers, and preferred compositions for these are also disclosed. These assemblies have potential use in delivery and encapsulation of therapeutic molecules. In particular, processes involving uptake of the assemblies by cells and release of therapeutic molecules from the assemblies. The inventive compositions are novel non-toxic drug carriers that have capability to form well-defined nanostructures and enter cells to deliver therapeutic cargos. The nanostructures can be reconfigured as a result of oxidation and reduction.

Methionine homopolymers, and random copolymers with other amino acids, have been previously described. Chemical modification of these polymers by oxidation (to yield either methionine sulfoxide or methionine sulfone residues) and alkylation (to yield either the methyl or carboxymethyl sulfonium salts of methionine residues) have also been described. These polymers are typically polydisperse (broad chain length distributions). Although preparation of thioether containing block copolypeptides, and their alkylation have been described earlier, preparation, assembly, or properties of resulting amphiphilic block copolypeptides and oxidation of the block copolymers is new. Furthermore, amphiphilic block copolypeptides containing hydrophilicly modified thioether containing residues have not been previously prepared. Self-assembly of methionine, or modified methionine, containing copolymers has also never been reported. Vesicle, micelle, emulsion or hydrogel formation with methionine containing copolymers has likewise never been reported. The ability to prepare well-defined methionine containing segments in block copolymers, and their chemical modification, now allows the preparation of functional, and biocompatible and bioresorbable polypeptide materials with potential for use in encapsulation and delivery of therapeutics, foods, cosmetics, and agricultural products, as surface coatings, as antimicrobials, as biomaterials such as tissue engineering scaffolds, as well as imaging and diagnostic applications.

BRIEF DESCRIPTIONS OF THE FIGURES

FIG. 1 shows chemical structures and schematic drawings of diblock copolypeptide, $M^O{}_{65}(L_{0.5}/F_{0.5})_{20}$ and its proposed self-assembly into vesicles.

FIG. 2 shows microscope images of a number of the self-assembled structures.

FIG. 4 shows LSCM images of cell uptake studies of HeLa cells incubated with vesicle suspensions containing 0 to 100% $R^H{}_{20}M^O{}_{55}(L_{0.5}/F_{0.5})_{20}$ mixed with $M^O{}_{65}(L_{0.5}/F_{0.5})_{20}$ polypeptide; FIG. 5 shows dye release experiments with FIG. 5A showing charts of dye release from block copolypeptide suspensions, $M^O{}_{65}(L_{0.5}/F_{0.5})_{20}$ vesicles, encapsulating Texas Red-labeled dextran incubated with MsrA and MsrB enzymes (dashed line, square data points) and with buffer only (short dashed-long dashed line and diamond-shaped data points) (dye release was determined by measuring absorbance and fluorescence of Texas Red)

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide synthesis of thioether-containing block polymer co-polypeptides.

General Methods and Materials Dry tetrahydrofuran (THF), hexane and diethyl ether were prepared by passage through alumina columns, and oxygen was removed by purging with nitrogen prior to use (1). Perkin Elmer RX1 FTIR Spectrophotometer was used for recording infrared spectra. 1H NMR spectra were recorded on a Bruker AVANCE 400 MHz spectrometer. Ultrapure (18 MΩ) water was obtained from a Millipore Milli-Q Biocel A10 purification unit.

Synthesis All α-amino acid-N-carboxyanhydride (NCA) monomers were synthesized using previously described protocols (2-4). L-Phenylalanine, L-leucine and Nε-trifluoroacetyl-L-lysine NCAs were synthesized by phosgenation and purified by recrystallization. Methionine monomer was prepared by a phosgenation and purified by column chromatography within a glovebox (5). α-Methoxy-ω-isocyanoethyl-poly(ethylene glycol)$_{45}$ (mPEG$_{45}$-NCO) was prepared by reacting α-methoxy-ω-aminoethyl-poly(ethylene glycol)$_{45}$ (mPEG$_{45}$-NH$_2$, Mn=2000 g mol-1; Nanocs, NY, N.Y.) with phosgene in THF for 16 hours (6). All block copolypeptides were synthesized using (PMe$_3$)$_4$Co initiator (7).

Determining Initiation Efficiency of L-Methionine-N-carboxyanhydride (Met NCA) with Initiator, (PMe$_3$)$_4$Co L-Methionine-N-carboxyanhydride (Met NCA) (60 mg, 0.34 mmol) was dissolved in THF (1.2 mL) and was separated into three vials containing equal volumes (0.11 mmol of NCA). To each vial, an aliquot of (PMe$_3$)$_4$Co initiator solution (100 μL, 50 μL, and 35 μL of a 20 mg/mL solution in THF) was added via syringe to give different monomer to initiator (M:I) ratios. The vials were sealed and allowed to stir in the glove box for 1 hour. An aliquot (20 μL) was removed from each polymerization solution and analyzed by FTIR to confirm that all Met NCA was consumed. In the glove box, α-methoxy-ω-isocyanoethyl-poly(ethylene glycol)$_{45}$ (mPEG$_{45}$-NCO) (65 mg) was dissolved in THF (2.6 mL) in a 20 mL scintillation vial. An aliquot solution of mPEG$_{45}$-NCO (1320 μL, 680 μL, and 480 μL of 25 mg/mL) was added to each polymerization solution containing different amounts of initiator (3 equiv per (PMe$_3$)$_4$Co, 0.006 mmol (PMe$_3$)$_4$Co, 0.003 mmol (PMe$_3$)$_4$Co, and 0.002 mmol (PMe$_3$)$_4$Co, respectively). The reactions were sealed and allowed to react overnight at room temperature. The reactions were removed from the glove box and HCl (2 equivalents per (PMe$_3$)$_4$Co, 6 M in H$_2$O) was added to the solution. After mixing, end-capped poly(L-methionine) (Mx-PEG$_{45}$) was collected by centrifugation. The solid was washed with water (3 times) to remove all unconjugated mPEG$_{45}$-NCO. Mx-PEG$_{45}$ was placed under high vacuum to remove residue H$_2$O before NMR analysis. Since it has been shown that end-capping is quantitative for (PMe$_3$)$_4$Co initiated NCA polymerizations when excess isocyanate is used (6) integrations of methionine resonances versus the polyethylene glycol resonance at δ3.64 could be used to obtain poly(L-methionine) lengths (8).

Preparation of poly(L-methionine) All polymerization reactions were performed in a nitrogen filled glovebox. To a solution of Met NCA in dry THF (50 mg/mL) was rapidly added, via syringe, a solution of (PMe$_3$)$_4$Co in dry THF (20 mM). The reaction was stirred at room temperature and polymerization progress was monitored by removing small aliquots for analysis by FTIR. Polymerization reactions were generally complete within 1 hour. Reactions were removed from the glove box and 6M HCl (2 equivalents per (PMe$_3$)$_4$Co) was added to the solution, which turned a blue-green color. After 10 min stirring, poly(Met) was collected by precipitation into acidic water (pH 3, HCl, >10× the reaction volume), followed by centrifugation. The white precipitate was washed with two portions of DI water and then lyophilized to yield poly(Met) as a fluffy white solid (99% yield). 1H NMR (500 MHz, d-TFA, 25 oC): δ5.07 (br s, 1H), 2.90 (br s, 2H), 2.48-2.29 (m, 5H).

Oxidation of poly(L-methionine) to give poly(L-methionine sulfoxide) Poly(Met) was suspended in (30% H$_2$O$_2$ in water with 1% acetic acid and stirred for 30 min at 0° C. (9). Full dissolution of the polymer was observed during this time to give a transparent homogeneous solution. The reaction was quenched with a few drops of 1M sodium thiosulfate in water, transferred to a 2000 MW cut off dialysis bag and dialyzed against DI water for 48 hours with water changes twice per day. The contents of the dialysis bag were then lyophilized to dryness (85% yield). 1H NMR (500 MHz, d-TFA, 25 oC): δ4.88 (br s, 1H) 3.51-3.13 (br m, 2H), 2.95 (br s, 3H), 2.67 (br s, 1 H), 2.44 (br s, 1 H).

Oxidation of poly(L-methionine) to give poly(L-methionine sulfone) Poly(Met) was suspended in 30% H$_2$O$_2$ in water with 1% acetic acid at 20° C. for 3 hrs. Full dissolution of the polymer was observed during this time to give a transparent homogeneous solution. The reaction was quenched with a few drops of 1M sodium thiosulfate in water, transferred to a 2000 MW cut off dialysis bag, and dialyzed against DI water for 48 hours with water changes twice per day. The contents of the dialysis bag were then lyophilized to dryness (85% yield). 1H NMR (500 MHz, d-TFA, 25° C.): δ4.59 (br s, 1 H) 3.89-3.43 (br m, 2H), 3.23 (br s, 3H), 2.94-2.44 (br m, 2H).

Synthesis of poly Poly(L-methionine)$_{60}$-block-poly(L-leucine$_{0.5}$-co-L-phenylalanine$_{0.5}$)$_{20}$, M$_{65}$(L$_{0.5}$/F$_{0.5}$)$_{20}$ L-Methionine-N-carboxyanhydride (Met NCA) (80 mg, 0.4 mmol) was dissolved in THF (1.6 mL) and placed in a 20 mL scintillation vial containing a stir bar. To the vial, (PMe$_3$)$_4$Co initiator solution (280 μL of a 20 mg/mL solution in THF) was added via syringe. The vial was sealed and allowed to stir in a glovebox for 1 hour. An aliquot (20 μL) was removed and analyzed by FTIR to confirm that all the NCA had been consumed. In the glovebox, mPEG$_{45}$-NCO (20 mg) was dissolved in THF (1 mL) in a 20 mL scintillation vial. An aliquot (240 μL) of the polymerization solution containing active chain ends was removed and added to the solution of PEG$_{45}$-isocyanate. The PEG end-capping solution vial was sealed and allowed to react for 24 hours. L-Leucine-N-carboxyanhydride (Leu NCA) (10.5 mg, 0.07 mmol) and L phenylalanine-N-carboxyanhydride (Phe NCA) (12.8 mg, 0.07 mmol) was dissolved in THF (210 μL and 260 μL, respectively), combined and added to the polymerization solution via syringe. The vial was sealed and allowed to stir in the glovebox for 1 hour to give the diblock M$_{65}$(L$_{0.5}$/F$_{0.5}$)$_{20}$. FTIR was used to confirm complete consumption of NCA. Outside of the glovebox, the PEG end-capped polypeptide (Mx-PEG$_{45}$) was isolated by precipitation using the previously described protocol. Outside the glovebox, the block copolypeptide was isolated by evaporating off all volatiles and dispersed in 10 mM HCl (3 times) to remove cobalt. The average composition of the copolymer as determined by 1H NMR integrations using end group analysis. Actual diblock copolypeptide composition M$_{66}$(L$_{0.5}$/F$_{0.5}$)$_{22}$.

Preparation of poly (L-methionine-sulfoxide)$_{65}$-block-poly(L-leucine$_{0.5}$-co-L-phenylalanine$_{0.5}$)$_{20}$, M$^O$$_{65}$(L$_{0.5}$/F$_{0.5}$)$_{20}$ In a 20 mL scintillation vial was charged with a stir bar, M$_{60}$(L$_{0.5}$/F$_{0.5}$)$_{20}$ (10 mg) was suspended in 30% H$_2$O$_2$ in water with 1% acetic acid and stirred for 30 min at 0° C.

The sample was diluted with water to twice its original volume. Saturated sodium thiosulfate was added drop wise to quench the peroxide, and the mixture was transferred to a 2000 MW cut-off dialysis bag and dialyzed against water for 2 days with frequent water changes.

The solution was lyophilized to dryness to yield a white solid. Yield 80%, loss is due to dialysis.

Determining Monomer to Initiator Ratio for Initiation Efficiency of Nε-trifluoroacetyl-L-lysine-N-carboxyanhydride (TFA-Lys NCA) with initiator, $(PMe_3)_4Co$ Nε-Trifluoroacetyl-L-lysine-N-carboxyanhydride (TFA-Lys NCA) (10-30 mg, mmol) was measured in three separate vials and dissolved in THF (50 mg NCA/mL THF). To each vial, a different amount of $(PMe_3)_4Co$ initiator solution (20 mg/mL solution in THF) was added via syringe to give different monomer to initiator (M:I) ratios of 5:1, 10:1 and 20:1. The vials were sealed and allowed to stir in the glovebox for 1 hour. An aliquot (20 μL) was removed from each polymerization solution and analyzed by FTIR to confirm that all TFA-Lys NCA had been consumed. In the glovebox, $mPEG_{45}$-NCO (87 mg) was dissolved in THF (3.5 mL) in a 20 mL scintillation vial. An aliquot solution of $mPEG_{45}$-NCO (2.2 mL, 920 μL, and 250 μL of 25 mg/mL) was added to each polymerization solution containing different amounts of initiator (3 equivalents per $(PMe_3)_4Co$, 9.0 mmol $(PMe_3)_4Co$, 4.6 mmol $(PMe_3)_4Co$, and 1.2 mmol $(PMe_3)_4Co$, respectively). The PEG end-capping solution vials were sealed and allowed to react for 24 hours. Outside of the glovebox, the PEG end-capped polypeptide poly(Nε-trifluoroacetyl-L-lysine)x-$PEG_{45}$ ((TFA)Kx-$PEG_{45}$) was isolated by precipitation using previously described protocol. (TFA)Kx-$PEG_{45}$ was placed under high vacuum to remove residual $H_2O$ before 1H NMR analysis. The degree of polymerization of each polypeptide was determined by 1H NMR integrations of Nε-trifluoroacetyl-L-lysine resonances versus the polyethylene glycol resonance at δ3.64.

Synthesis of poly(NE-trifluoroacetyl-L-lysine)$_{10}$-block-poly(L-methionine)$_{55}$-block-poly(L-leucine$_{0.5}$-co-L-phenylalanine$_{0.5}$)$_{20}$, (TFA) $K_{10}M_{55}(L_{0.5}/F_{0.5})_{20}$ Nε-trifluoroacetyl-L-lysine-N-carboxyanhydride (TFA-Lys NCA) (20 mg, 0.076 mmol) was dissolved in THF (410 μL) in a 20 mL scintillation vial. To the vial, $(PMe_3)_4Co$ initiator solution (380 μL of a 20 mg/mL solution in THF) was added via syringe. The vial was sealed and allowed to stir in the glovebox for 1 hour. An aliquot (20 μL) was removed and analyzed by FTIR to confirm that all TFA-Lys NCA had been consumed. In the glovebox, L-methionine-N-carboxyanhydride (Met NCA) was measured in a separate vial (80 mg, 0.46 mmol) and dissolved in THF (1.60 mL). The Met NCA solution was added to the polymerization mixture via syringe. The vial was sealed and allowed to stir in the glovebox for 1 hour. An aliquot (20 μL) was removed and analyzed by FTIR to confirm that all Met NCA had been consumed. In the glovebox, $mPEG_{45}$-NCO (12 mg) was dissolved in THF (0.5 mL) in a 20 mL scintillation vial. An aliquot (240 μL) of the polymerization solution containing active chain ends (0.002 mmol) was removed and added to the solution of $mPEG_{45}$-NCO. The PEG end-capping solution vial was sealed and allowed to react for 24 hours. L-Leucine-N-carboxyanhydride (11 mg, 0.07 mmol) and L-phenylalanine-N-carboxyanhydride (13 mg, 0.07 mmol) were dissolved in THF (222 μL and 270 μL, respectively), combined and added to the polymerization solution via syringe. The vial was sealed and allowed to stir in the glovebox for 1 hour to give the triblock copolypeptide (TFA)$K_{10}M_{55}(L_{0.5}/F_{0.5})_{20}$. FTIR was used to confirm complete consumption of NCA. Outside of the glovebox, the PEG end-capped polypeptide ((TFA)$K_xM_y$-$PEG_{45}$) was isolated by precipitation to remove excess mPEG-NCO. (TFA)$K_xM_y$-$PEG_{45}$ was placed under high vacuum to remove residue $H_2O$ before using 1H NMR to determine length of each block. Outside the glovebox, the triblock copolypeptide was isolated by evaporating off all volatiles and dispersed in 10 mM HCl (3 times) to remove cobalt. The degree of polymerization of the polypeptide was determined by 1H NMR integrations of Nε-trifluoroacetyl-L-lysine resonances and L-methionine resonances versus the polyethylene glycol resonance at δ3.64. Actual composition (TFA)K 11M55 (L0.5/F0.5)18.

Synthesis of poly(Nε-trifluoroacetyl-L-lysine)$_{20}$-block-poly(L-methionine)$_{55}$-block-poly(L-leucine$_{0.5}$-co-L-phenylalanine$_{0.5}$)$_{20}$, (TFA) $K_{20}M_{55}(L_{0.5}/F_{0.5})_{20}$ Nε-Trifluoroacetyl-L-lysine-N-carboxyanhydride (TFA-K NCA) (50 mg, 0.185 mmol) was dissolved in THF (1 mL) in a 20 mL scintillation vial. To the vial, $(PMe_3)_4Co$ initiator solution (463 μL of a 20 mg/mL solution in THF) was added via syringe. The vial was sealed and allowed to stir in the glovebox for 1 hour. An aliquot (20 μL) was removed and analyzed by FTIR to confirm that all TFA-K NCA had been consumed. In the glovebox, L-methionine-N-carboxyanhydride (Met NCA) was measure in a separate vial (98 mg, 0.556 mmol) and dissolved in THF (1.96 mL). The Met NCA solution was added to the polymerization mixture vial syringe. The vial was sealed and allowed to stir in the glovebox for 1 hour. An aliquot (20 μL) was removed and analyzed by FTIR to confirm that all Met NCA had been consumed. In the glovebox, $PEG_{45}$-isocyanate (10 mg) was dissolved in THF (0.350 mL) in a 20 mL scintillation vial. An aliquot (230 μL) of the polymerization solution containing active chain ends (0.0017 mmol) was removed and added to the solution of $PEG_{45}$-isocyanate. The PEG end-capping solution vial was sealed and allowed to react for 24 hours. L-Leucine-N-carboxyanhydride (Leu NCA) (14 mg, 0.09 mmol) and L-phenylalanine-N-carboxyanhydride (Phe NCA) (17 mg, 0.09 mmol) were dissolved in THF (280 μL and 340 μL, respectively), combined and added to the polymerization solution via syringe. The vial was sealed and allowed to stir in the glovebox for 1 hour to give the triblock (TFA) $K_{20}M_{55}(L_{0.5}/F_{0.5})_{20}$. FTIR was used to confirm complete consumption of NCA. Outside of the dry box, the PEG end-capped polypeptide ((TFA)$K_xM_y$-$PEG_{45}$) was isolated by precipitation to remove excess mPEG-NCO. (TFA)$K_xM_y$-$PEG_{45}$ was placed under high vacuum to remove residue $H_2O$ before using 1H NMR to determine length of each block. Outside the glovebox, the triblock copolypeptide was isolated by evaporating off all volatiles and dispersed in 10 mM HCl (3 times) to remove cobalt. The degree of polymerization of the polypeptide was determined by 1H NMR integrations of Nε-trifluoroacetyl-L-lysine resonances and L-methionine resonances versus the polyethylene glycol resonance at δ3.64. Actual composition (TFA)$K_{21}M_{54}(L_{0.5}/F_{0.5})_{18}$.

Preparation to poly (Nε-trifluoroacetyl-L-lysine)$_x$-block-poly(L-methionine sulfoxide)$_{55}$-block-poly-(L-leucine$_{0.5}$-co-L-phenylalanine$_{0.5}$)$_{20}$ (x=11, 21), (TFA)$K_xM^O_{55}(L_{0.5}/F_{0.5})_{20}$: In a 20 mL scintillation vial was charged with a stir bar, (TFA)$K_xM^O_{55}(L_{0.5}/F_{0.5})_{20}$ (10 mg) was suspended in 30% $H_2O_2$ in water with 1% acetic acid and stirred for 30 min at 0° C. The sample was diluted with water to twice its original volume. Saturated sodium thiosulfate was added drop wise to quench the peroxide, and the mixture was transferred to a 2000 MW cut off dialysis bag and dialyzed against Millipore water for 2 days with frequent water changes. The solution was lyophilized to dryness to yield a white solid. Yield >80%, loss is due to dialysis.

Deprotection of Trifluoroacetyl Groups The protected triblock polypeptide, (TFA) $K_{10}M^O_{55}(L_{0.5}/F_{0.5})_{20}$ or $K(TFA)_{20}M^O_{55}(L_{0.5}/F_{0.5})_{20}$, was dispersed in a 1:20 (v/v) solution of $H_2O$ to methanol (5 mg/mL) containing 60 mM $K_2CO_3$ (10). The suspension was heated to reflux. After 4 hours, the reaction mixture was allowed to cool to room temperature and the solvent was removed under high vacuum. The solid was dispersed in water and transferred to a dialysis bag (2000 MWCO) and dialyzed against 10 mM HCl and NaCl for 24 hours with 3 changes of water and then against Millipore water for 24 hours with 3 water changes. The polypeptide solution was lyophilized to yield a white solid. Yield >80%, loss is due to dialysis.

Preparation of poly (L-homoarginine)$_x$-block-poly(L-methionine sulfoxide)$_{55}$-block-poly(L-leucine$_{0.5}$-co-L-phenylalanine$_{0.5}$)$_{20}$, $R^H_x M^O_{55}(L_{0.5}/F_{0.5})^{20}$ (x=10, 20) The polypeptide sample, $K_x M^O_{55}(L_{0.5}/F_{0.5})_{20}$ (from the previous reaction), was dispersed in aqueous NaOH (10 mg/ml, 1 mM) in a plastic 15 mL conical tube. The guanylating reagent, 3,5-dimethylpyrazole-1-carboxamidine nitrate (10 equiv. per each lysyl amine group), was dissolved in aqueous 1 M NaOH and added to the polypeptide suspension. The reaction mixture was sealed and placed in a bath sonicator for 1 minute and then placed in an oven at 37° C. for 72 hours. After 72 h, the reaction mixture was acidified to pH of 3 with HCl and placed in a dialysis bag (MWCO=2000 Da) and dialyzed against aqueous NaCl (10 mM, 2 days) and Millipore water (2 days), changing each solution 3 times/day. The polypeptide was isolated by lyophilizing the solution. The typical guanylation efficiency is ca. 90%, and isolated yields ranged from 85 to 95%.

Circular Dichroism of Polypeptides: Circular Dichroism spectra (190-250 nm) were recorded in a quartz cuvette of 0.1 cm path length with samples prepared at concentrations of 0.10 to 0.25 mg/mL using Millipore deionized water. All spectra were recorded as an average of 3 scans. The spectra are reported in units of molar ellipticity [θ] (deg·cm$^2$·dmol$^{-1}$). The formula used for calculating molar ellipticity, [θ], was [θ]=(θ×100×$M_W$)/(c×l) where θ is the experimental ellipticity in millidegrees, $M_W$ is the average molecular weight of a residue in g/mol, c is the peptide concentration in mg/mL; and l is the cuvette pathlength in cm. The percent α-helical content of the peptides was estimated using the formula % α-helix=100x(-[θ]$_{222nm}$+3000)/39000) where [θ]$_{222nm}$ is the measured molar ellipticity at 222 nm (11). Using this estimation, poly(Met$^{O2}$)$_{80}$ is 99% α-helical in deionized water, 20° C.

Fluorescent Probe Modification of Diblock Polypeptide: 5-(Iodoacetamido)fluorescein was conjugated to the thioether of the methionine side chains using the previous alkylation method. The polypeptide $M_{65}(L_{0.5}/F_{0.5})_{20}$ (10 mg) was dissolved in DMF (1 mL) in a 20 mL scintillation vial. 5-(Iodoacetamido)fluorescein was dissolved in DMF (10 mg/mL) and added to the a 1% (w/v) polypeptide solution a 5:1 molar ratio to the polypeptide chains. After fluorescein modification, the remaining methionine residues were then oxidized to methionine sulfoxides as described above.

Fluorescent Probe Modification of Triblock Polypeptide: Fluorescein isothiocyanate (FITC) or rhodamine isothiocyanate (TRITC) was conjugated to the amino group of the lysine side chains in triblock copolypeptides. The polypeptide $K_x M_{55}(L_{0.5}/F_{0.5})_{20}$ (x=10, 20, 10 mg) was dispersed in sodium carbonate buffer at pH 8.0 (1 mL) in a 15 mL conical tube. FITC or TRITC (0.2 equivalent to 1 equivalent of the polypeptide) was dissolved in dry DMSO (10 mg/mL) and was added to the polymer solution. The conjugation was allowed to proceed overnight. The resulting copolypeptide solution was dialyzed (8,000 MWCO membrane) against Millipore water for 2 days, changing the water 3 times/day. The purified polypeptide was isolated by lyophilization to yield 1 fluorescent molecule per 5 chains of polypeptide.

Preparation of Polypeptide Assemblies Solid polypeptide powder ($M^O_{65}(L_{0.5}/F_{0.5})_{20}$, $R^H_{10}M^O_{55}(L_{0.5}/F_{0.5})_{20}$, $R^H_{20}M^O_{55}(L_{0.5}/F_{0.5})_{20}$) was dispersed in THF to give a 1% (w/v) suspension. The suspension was placed in a bath sonicator for 30 minutes to evenly disperse the polypeptide and reduce large particulates. An equivalent amount of Millipore water was then added to give a 0.5% (w/v) suspension. The suspension became clear as the solution was mixed by vortex. The mixture was then dialyzed (2,000 MWCO membrane) against Millipore water overnight with changing the water 3 times. The THF can also be removed by evaporation resulting in vesicular assemblies.

Figure 1A:
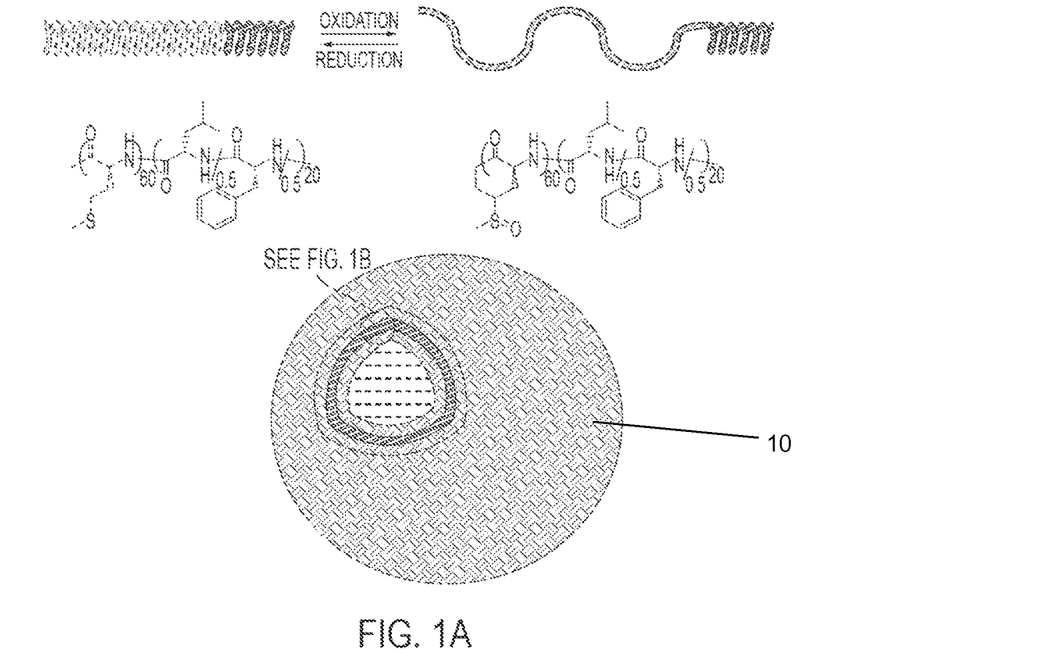
FIG. 1A shows chemical structures, tertiary peptide structure and a vesicle.
Figure 1B:
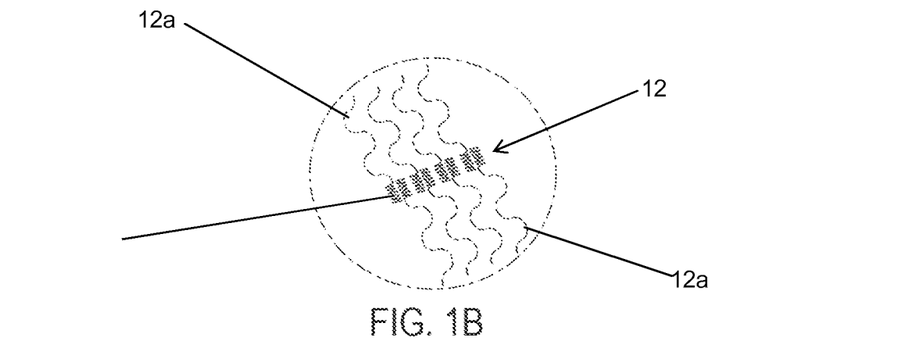
FIG. 1B shows the orientation of the molecules in a cross-section of a vesicle wall.
Figure 2A:
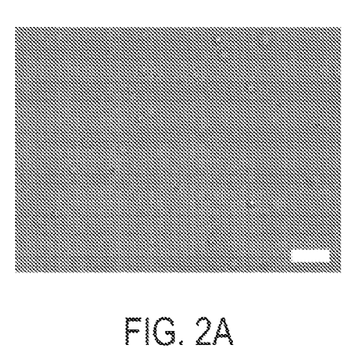
FIG. 2A shows a differential interference contrast (DIC) image of $M^O{}_{65}(L_{0.5}/F_{0.5})_{20}$.

Self-assembly of Polypeptide Vesicles Containing Both Diblock and Triblock Polypeptides Solid diblock polypeptide powder ($M^O_{65}(L_{0.5}/F_{0.5})_{20}$) and triblock polypeptide powder ($R^H_{10}M^O_{55}(L_{0.5}/F_{0.5})_{20}$ or $R^H_{20}M^O_{55}(L_{0.5}/F_{0.5})_{20}$) were dispersed separately in THF to give a 1% (w/v) suspensions. The suspensions were placed in a bath sonicator for 30 minutes to evenly disperse the polypeptides and reduce large particulates. An equivalent amount of Millipore water was then added to give 0.5% (w/v) suspensions. The suspensions became clear as the solution was mixed by vortex. Aliquots of triblock and diblock (25:75, 50:50 and 75:25 (w/w) triblock to diblock) were mixed and then placed in bath sonicator for 30 min to evenly distribute. The mixture was then dialyzed (2,000 MWCO membrane) against Millipore water overnight with changing the water 3 times. The THF can also be removed by evaporation resulting in vesicular assemblies. FIG. 1A diagrammatically represents a vesicle 10 that is formed from the triblock peptides 12 that shows three molecular regions (see FIG. 1B). Either end 12a of the peptides are hydrophilic while the center portion 12b of each molecule is hydrophobic. When a vesicle is formed, the molecules self-assemble so that the hydrophobic regions are located within the center of the vesicle wall while the hydrophilic regions contact the aqueous milieu within and surrounding the vesicle Differential Interference Microscopy (DIC) Suspensions of the copolypeptides, ($M^O_{65}(L_{0.5}/F_{0.5})_{20}$, $R^H_{10}M^O_{55}(L_{0.5}/F_{0.5})_{20}$ or $R^H_{20}M^O_{55}(L_{0.5}/F_{0.5})_{20}$, (0.5% (w/v)) were visualized on glass slides with a spacer between the slide and the coverslip (double-sided tape or Secure Seal Imaging Spacer, Grace Bio-labs) allowing the self-assembled structures to be minimally disturbed during focusing. The samples are imaged using a Zeiss Axiovert 200 DIC/Fluorescence Inverted Optical Microscope. FIG. 2A shows a DIC view of such vesicles.

Extrusion of Polypeptide Assemblies The aqueous vesicle suspension of $M^O_{65}(L_{0.5}/F_{0.5})_{20}$, $R^H_{10}M^O_{55}(L_{0.5}/F_{0.5})_{20}$ or $R^H_{20}M^O_{55}(L_{0.5}/F_{0.5})_{20}$, diluted to 0.2% (w/v) was extruded using an Avanti Mini-Extruder. Extrusions were performed using different pore sizes (Whatman Nuceleopore Track-Etched polycarbonate (PC) membranes), following a protocol of serial extrusions of vesicles through decreasing filter pore sizes: 3 times through a 1.0 µm filter, 3 times through 0.4 µm filter, 3 times through 0.2 µm filter, and 3 times through 0.1 µm filter. The PC membranes and filter supports are soaked in Millipore water for 10 minutes prior to extrusion.

Dynamic Light Scattering (DLS) of Extruded Vesicles The 0.2% (w/v) of extruded polypeptide suspensions, $M^O{}_{65}(L_{0.5}/F_{0.5})_{20}$, $R^H{}_{10}M^O{}_{55}(L_{0.5}/F_{0.5})_{20}$ or $R^H{}_{20}M^O{}_{55}(L_{0.5}/F_{0.5})_{20}$, were placed in a disposable cuvette and analyzed with the Malvern Zetasizer Nano ZS model Zen 3600 (Malvern Instruments Inc, Westborough, Mass.). A total scattering intensity of approximately $1\times10^5$ cps was targeted. The autocorrelation data was fitted using the CONTIN algorithm to determine the diameters of suspended assemblies.

Zeta Potential of Polypeptide Assemblies A 0.5% (w/v) suspension of copolypeptide vesicles, $M^O{}_{65}(L_{0.5}/F_{0.5})_{20}$ was diluted to 0.2% (w/v) with Millipore water containing NaCl to give a final concentration of 10 mM salt. The pH was then adjusted using NaOH or HCl to give acidic to basic solutions ranging from pH 3 to 8. The solution was added to a disposable capillary cell (Malvern Instruments Inc, Westborough, Mass.). The zeta potential was analyzed with the Malvern Zetasizer Nano ZS model Zen 3600 (Malvern Instruments Inc, Westborough, Mass.).

Figure 2B:
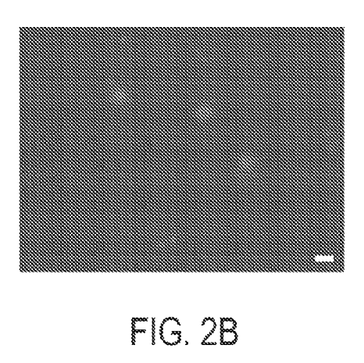
FIG. 2B shows a laser scanning confocal microscopy (LSCM) image of fluorescein labeled $M^O{}_{65}(L_{0.5}/F_{0.5})_{20}$.
Figure 2C:
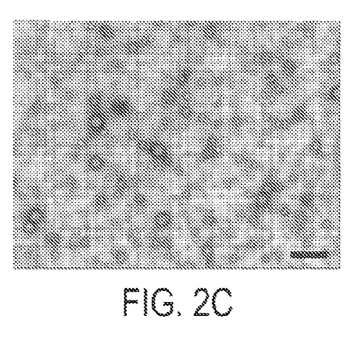
FIG. 2C shows images of extruded suspension of $M^O{}_{65}(L_{0.5}/F_{0.5})_{20}$ by transmission electron microscopy (TEM)
Figure 2D:
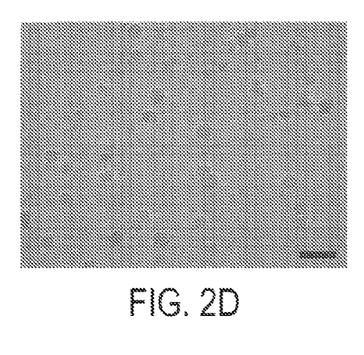
FIG. 2D shows images of extruded suspension of $M^O{}_{65}(L_{0.5}/F_{0.5})_{20}$ by cryo-electron microscopy.
Figure 2E:
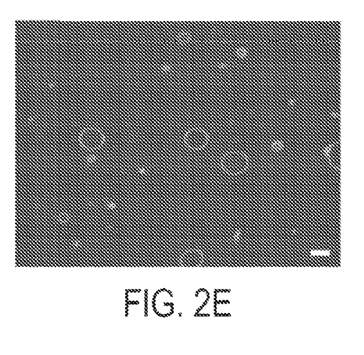
FIGS. 2E and 2F show an LSCM z-series image of 1% (w/v) aqueous suspensions of 25% TRITC-labeled $R^H{}_{10}M^O{}_{55}(L_{0.5}/F_{0.5})$ and 75% FITC-labeled $M^O{}_{65}(L_{0.5}/F_{0.5})_{20}$ with FIG. 2E showing the FITC channel and FIG. 2F showing the TRITC channel; the bars represent 5 µm for panels A,B,E and F; the bars represent 200 nm for panels C and D)
Figure 2F:
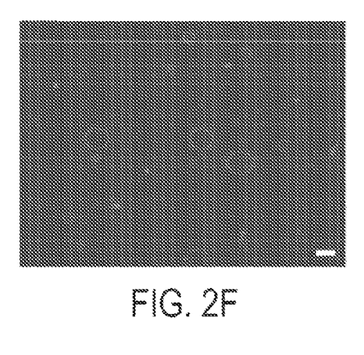

Laser Scanning Confocal Microscopy (LSCM) of Fluorescently Labeled Vesicles LSCM images of the vesicles were taken on a Leica Inverted TCS-SP1 MP-Inverted Confocal and Multiphoton Microscope equipped with an argon laser (476 and 488 nm blue lines), a diode (DPSS) laser (561 nm yellow-green line), and a helium-neon laser (633 nm far red line). Suspensions of the fluorescently labeled copolypeptides (0.5% (w/v)) were visualized on glass slides with a spacer between the slide and the cover slip (Secure Seal Imaging Spacer, Grace Bio-labs) allowing the self-assembled structures to be minimally disturbed during focusing. Imaging of an x-y plane with an optical z-slice showed that the assemblies were water-filled, unilamellar vesicles. FIG. 2B shows an LSCM image of vesicles. FIGS. 2E and 2F show the FITC and TRITC images, respectively, of vesicles made from a mixture of FITC and TRITC labeled polymers. Note that all vesicles are labeled in either view demonstrating that the differently labeled polymers mix and do not segregate.

Transmission Electron Microscopy (TEM) of Extruded Vesicles The extruded aqueous copolypeptide suspensions were diluted to give 0.1% (w/v). The sample (4 μL) was placed on a 300 mesh Formvar/carbon coated copper grid (Ted Pella) and allowed to remain on the grid for 60 seconds. Filter paper was used to remove the residual sample. One drop of 2% (w/v) uranyl acetate (negative stain) was then placed on the grid for 90 seconds, and subsequently removed by washing with drops of Millipore water and removing the excess liquid with filter paper. The grids containing sample were allowed to dry before imaging with JEM 1200-EX (JEOL) transmission electron microscope at 80 kV. FIG. 2C shows such negatively-stained vesicles.

Cryogenic Electron Microscopy of Extruded Vesicles A drop of 0.2% (w/v) extruded aqueous copolypeptide suspension was placed on a 300 mesh copper grid containing a Quantifoil holey carbon film (SPI Supplies, West Chester, Pa.). The sample was allowed to remain on the grid for 30 seconds and was blotted with filter paper and quickly placed in a cryogenic bath containing liquid ethane. The grid was stored under liquid nitrogen and then placed, using a cold stage, in a TF20 (FEI Tecnai G2) electron microscope and imaged with an accelerating voltage of 200 kV. FIG. 2D shows vesicles imaged in this manner. Sample preparation and imaging was performed at the Electron Imaging Center for Nanomachines (EICN) established at the California NanoSystems Institute (CNSI).

Bradford Assay with Polypeptide Vesicle Bradford assay was performed to quantify the final concentration of the polypeptide vesicles after extrusion according to the manufacture supplied instructions, using the predialyzed samples as the standard.

Cell Culture The HeLa cell line was grown in Minimal Essential Medium supplemented with 26.2 mM sodium bicarbonate, 1 mM sodium pyruvate, 10% FBS, and 1% penicillin/streptomycin, at a pH of 7.4. The cell line is maintained in a 37° C. humidified atmosphere with 5% CO2 and handled with standard sterile tissue culture protocols.

Figure 4A:
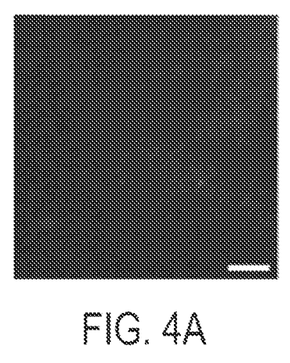
FIG. 4A shows cells only.
Figure 4B:
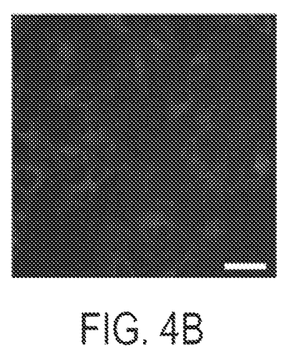
FIG. 4B $M^O{}_{65}(L_{0.5}/F_{0.5})_{20}$.
Figure 4C:
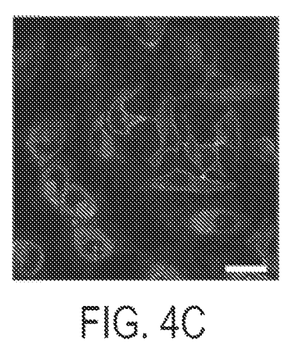
FIG. 4C shows 25% $R^H{}_{20}M^O{}_{55}(L_{0.5}/F_{0.5})_{20}$.
Figure 4D:
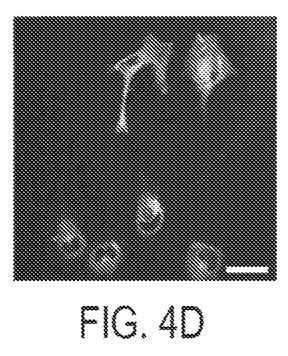
FIG. 4D shows 50% $R^H{}_{20}M^O{}_{55}(L_{0.5}/F_{0.5})_{20}$.
Figure 4E:
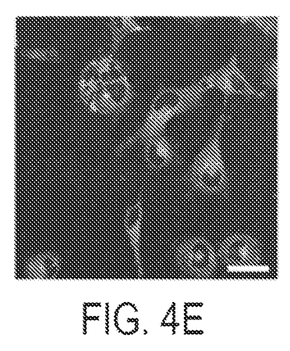
FIG. 4E shows 75% $R^H{}_{20}M^O{}_{55}(L_{0.5}/F_{0.5})_{20}$.
Figure 4F:
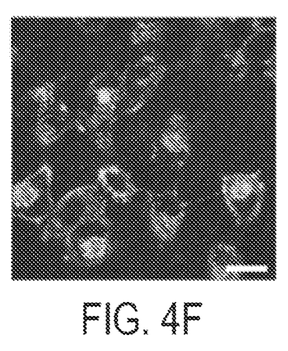
FIG. 4F shows 100% $R^H{}_{20}M^O{}_{55}(L_{0.5}/F_{0.5})_{20}$ (scale bar=20 µm, all figures)

Vesicle Uptake HeLa cells were seeded at a density of $5\times10^5$ cells/cm$^2$ and incubated overnight prior to the experiment. The cells were seeded onto 8-well chambered cover glassed for confocal microscopy experiments and 35 mm tissue culture plates for flow cytometry. On the day of the experiment, different fluorescently-labeled vesicles were separately diluted in serum-free media and incubated with HeLa cells for 5 hrs to allow the vesicles to be internalized by the cells. Subsequently, the medium containing the vesicles was aspirated, and the cells were washed three times with PBS to remove nonspecifically attached peptides on the cell surface. Afterwards, the cells are subjected to either confocal microscopy or flow cytometry to determine the extent of vesicle uptake. FIG. 4 shows the microscopic results of uptake. FIG. 4A shows the cells alone. The remaining panels show HeLa cell structures illuminated by uptake of various fluorescently labeled vesicles.

Laser Scanning Confocal Microscopy (LSCM) of Cells The LSCM images of the cells were taken on a Leica Inverted TCS-SP MP Spectral Confocal and Multiphoton Microscope (Heidelberg, Germany) equipped with an argon laser (488 nm blue excitation: JDS Uniphase), a diode laser (DPSS; 561 nm yellow-green excitation: Melles Griot), a helium-neon laser (633 nm red excitation), and a two photon laser setup consisting of a Spectra-Physics Millenia X 532 nm green diode pump laser and a Tsunami Ti-Sapphire picosecond pulsed infrared laser tuned at 768 nm for UV excitation.

Flow Cytometry Flow cytometry analysis of HeLa cells incubated with the vesicles were performed on a BD FACScan™ (BD Bioscience, San Jose, Calif.) system equipped with an argon laser (488 nm blue excitation) and two filters: a green filter (530±30 nm) and an orange filter (585±42 nm). A total of 10,000 cells per sample were used for the analysis. The mean fluorescence intensity was used as a metric to represent the degree of vesicle internalization into the cells.

Figure 3:
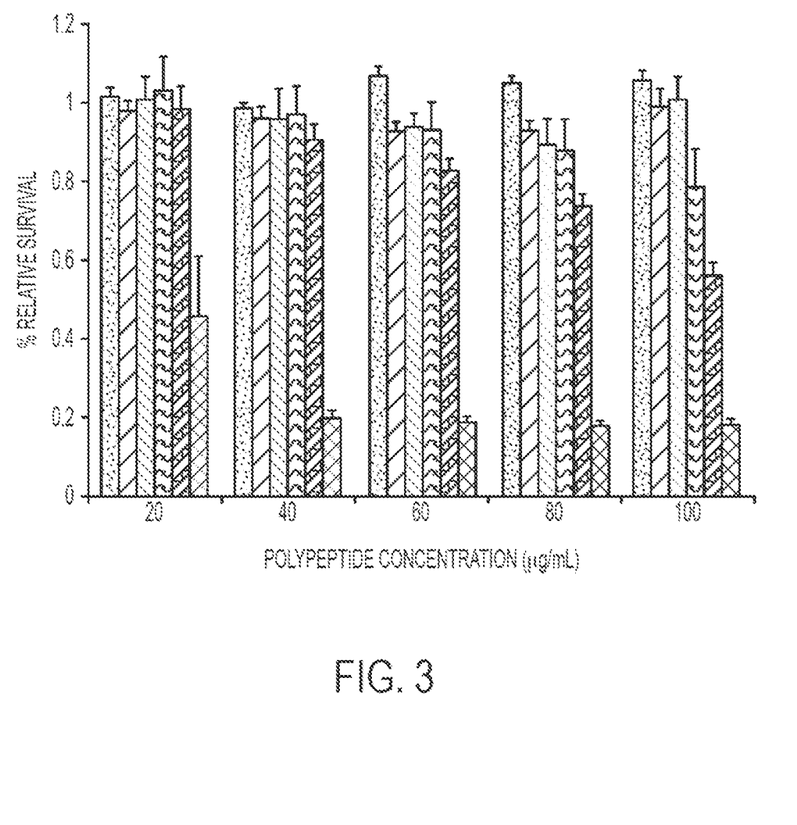
FIG. 3 shows MTS cell survival data after 5 hr incubation for HeLa cells separately incubated with aqueous suspensions of (stippled) $M^O{}_{65}(L_{0.5}/F_{0.5})_{20}$; (solid diagonal lining) 50% $R^H{}_{10}M^O{}_{55}(L_{0.5}/F_{0.5})_{20}$ and 50% $M^O{}_{65}(L_{0.5}/F_{0.5})_{20}$; (dotted diagonal lining) 50% $R^H{}_{20}M^O{}_{55}(L_{0.5}/F_{0.5})_{20}$ and 50% $M^O{}_{65}(L_{0.5}/F_{0.5})_{20}$; (curved diagonal lining) $R^H{}_{10}M^O{}_{55}(L_{0.5}/F_{0.5})_{20}$; (striped diagonal lining) $R^H{}_{20}M^O{}_{55}(L_{0.5}/F_{0.5})20$; and (diamond pattern) $R^H{}_{60}L_{20}$.

Measurement of Cytotoxicity using the MTS Cell Proliferation Assay The MTS cell proliferation assay (CellTiter 96® AQueous Non-Radioactive Cell Proliferation Assay) was performed to assess the cytotoxicity level of the vesicles. The uptake experiments were performed with HeLa cells seeded on 96-well plates with triplicates of each condition. After the 5-hr incubation period, the medium was aspirated and fresh medium containing 20% MTS reagent was added to the cells. The cells were incubated again at 37° C. for 1 hr, and the absorbances at 490 nm and 700 nm were measured using the Infinite F200 plate reader (Tecan Systems Incorporated, San Jose, Calif.). The relative survival of cells compared to control cells (i.e., cells incubated in growth medium without vesicles) was calculated by determining the ratio of the (A490-A700) values. FIG. 3 shows the survival rate resulting from different uptake of vesicles of differing composition. Generally, the polymers with large blocks of homoarginine tend to result in reduced cellular survival while most of the polymers were well tolerated.

Chemical Reduction of Poly(L-methionine sulfoxide) Homopolypeptide, poly(L-methionine sulfoxide), was dissolved in Millipore water containing thioglycolic acid (750 mM) to give a 0.1% (w/v) solution (12). The solution was allowed to react for 20 hours at 37 °C. The solution was dialyzed (2,000 MW cut off membrane) for 3 days against Millipore water, changing the water 3 times/day. The dialyzed polymer was isolated by lyophilization to yield a white powder. Yield >80%, loss is due to dialysis.

Chemical Reduction of Polypeptide Vesicles Thioglycolic acid (0.05 mmol) was added to a 0.5% (w/v) suspension of $M^O{}_{65}$ ($L_{0.5}/F_{0.5}$)$_{20}$ (20 µL) to give a concentration 750 mM. The solution was allowed to react at 37° C. for 40 min. The solution was imaged using DIC before and after the reduction to monitor the vesicular morphology. A 0.5% (w/v) suspension of $K_{60}L_{20}$ (20 µL) was used as a control for reduction with thioglycolic acid. FIG. 1A shows this effect diagrammatically. The drawings represents the diblock polymer as being a coil in solution. Note that the chemical diagram shows the chemical composition of the 60mer and 20mer blocks of the polymer, When the polymer is subjected to oxidation (right side of the diagram) the thioether groups become oxidized and that portion of the polymer relaxes. The 20mer block is not subject to oxidation under these conditions and does not change.

Enzyme Reduction of Polypeptide Vesicles A 1% (w/v) suspension of copolypeptide vesicles, $M^O{}_{65}$ ($L_{0.5}/F_{0.5}$)$_{20}$ was diluted to 0.1% (w/v) with Millipore water containing 20 mM Tris-HCl, 10 mM MgCl2, 30 mM KCl, 20 mM DTT and 1 µg of each Methionine sulfoxide reductase A and Methionine sulfoxide reductase B (Prospec-Tany TechnoGene Ltd. Ness Ziona, Israel) (13). A control sample was prepared as above without the addition of enzymes. The suspensions were placed in a 37° C. water bath for 16 hrs. The suspensions were then visualized by differential interference contrast microscopy (DIC).

Dye Encapsulation in Polypeptide Vesicles The diblock copolypeptide, $M^O{}_{65}$ ($L_{0.5}/F_{0.5}$)$_{20}$, sample was dispersed in THF to give 1% (w/v) suspensions, which were then placed in a bath sonicator for 30 minutes until the copolypeptides were evenly dispersed. An equal volume of Millipore water containing Texas Red labeled dextran (Molecular Probes, MW=3000, 0.25 mg/mL) was added to the suspension to give final sample concentrations of 0.5% (w/v), which was then placed in a bath sonicator for 30 minutes. The THF was removed by evaporation. After 24 hours, the suspension was transferred to a dialysis bag (MWCO=8000 Da) to remove all dextran that was not encapsulated by the vesicles. The water was changed every hour for the first 4 hours. For enzyme reduction studies the sample was dialyzed against a buffered solution (20 mM Tris-HCl, 10 mM MgCl2, 30 mM KCl) prior to dye release studies.

Figure 5A:
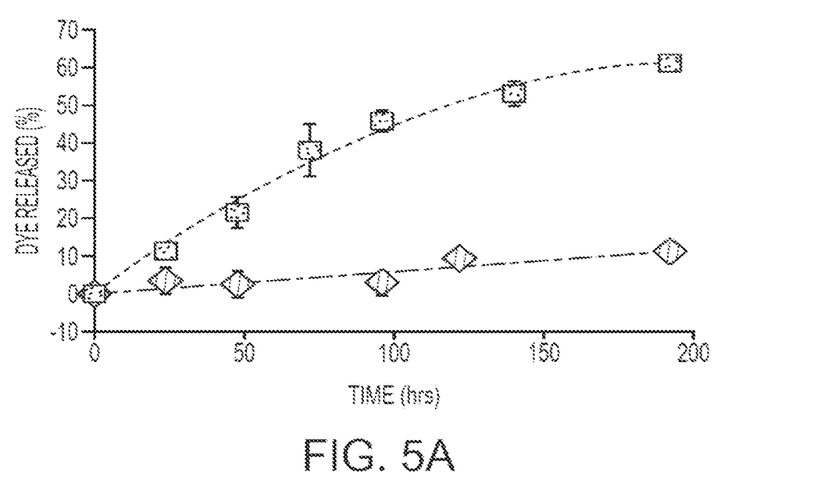

Dye Leakage of Enzymatically Reduced Polypeptide Vesicles A 1% (w/v) suspension of copolypeptide vesicles, $M^O{}_{65}$ ($L_{0.5}/F_{0.5}$)$_{20}$ with encapsulated Texas Red labeled dextran, was diluted to 0.1% (w/v) with Millipore water containing 20 mM Tris-HCl, 10 mM MgCl2, 30 mM KCl, 20 mM DTT and 1 µg of each Methionine sulfoxide reductase A and Methionine sulfoxide reductase B (Prospec-Tany TechnoGene Ltd. Ness Ziona, Israel). The diluted suspension (1 mL) was added to an 8000 MWCO dialysis bag and dialyzed against 20 mM Tris-HCl, 10 mM MgCl2, 30 mM KCl, 20 mM DTT (250 mL). An aliquot (20 µL) was removed from the dialysis bag at different time points. DMSO (180 µL) was added to each aliquot and the suspension was sonicated before the excitation (589 nm) and emission (615 nm) was read on a QuantaMaster 40 UV Vis spectrofluorometer (Photon Technology International Inc., Birmingham, N.J.). FIG. 5A shows that in the presence of the enzymes (square data points) considerably more dye is released from the vesicles than in the presence of buffer only (diamond-shaped data points).

Figure 5B:
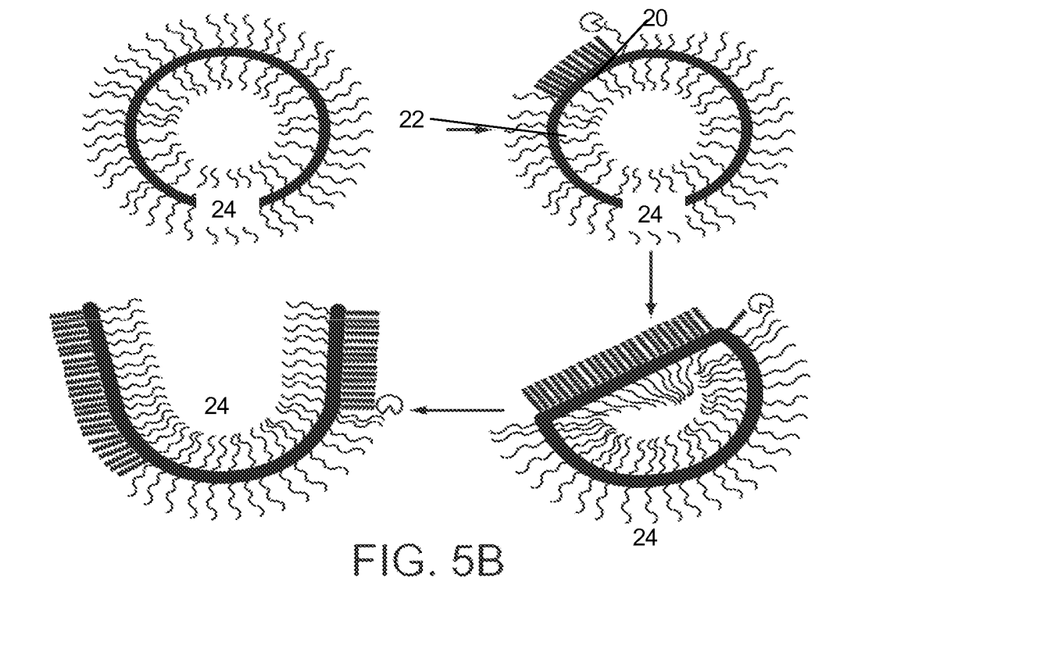
FIG. 5B shows a schematic diagram of a possible mechanism of dye release in the presence of Msr reductases.

FIG. 5B presents a diagrammatic explanation of the phenomenon of dye release. When the reductase enzyme 20 reduces the hydrophilic portion of the polymer (refer to FIG. 1 and related text), that portion changes into a more coiled configuration 22. Because the enzyme 20 is unable to penetrate into the vesicle, all reduction takes place on the exterior surface of the vesicle. The coiled portions of the polymer interact laterally setting up a rigid, flattened portion of the vesicle membrane. Eventually, when this rigid area becomes too large, the strain causes the vesicle to rupture and release the enclosed dye 24.

Protease Degradation of Poly(L-methionine sulfoxide) A sample of poly(L-methionine sulfoxide)$_{265}$-block-poly(ethylene glycol)$_{45}$ (0.1 µmol, 28 µmol) $M^O$) was dissolved in Millipore water containing 50 mM Tris-HCl and 5 mM CaCl$_2$ (1 mL). After the polypeptide was completely soluble, Proteinase K (0.0036 µmol, Aldrich) was added to the solution and placed in a 37° C. water bath and allowed to react for 24 hrs. After 24 hours, EDTA was added to the solution to stop the degradation. The solution was added to a dialysis bag (1000 MW cut off) and dialyzed against water to remove EDTA and Calcium from the solution. The sample was freeze-dried to yield a white solid (poly (ethylene glycol)$_{45}$).

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

REFERENCES (1) Pangborn, A. B.; Giardello, M. A.; Grubbs, R. H.; Rosen, R. K.; Timmers, F. J. Organometallics 1996, 15, 1518.
(2) Fuller, W. D.; Verlander, M. S.; Goodman, M. Biopolymers 1976, 15, 1869.
(3) Deming, T. J. Nature 1997, 390, 386.
(4) Kricheldorf, H. R. Angewandte Chemie International Edition 2006, 45, 5752.
(5) Kramer, J. R.; Deming, T. J. Biomacromolecules 2010, null.
(6) Brzezinska, K. R.; Curtin, S. A.; Deming, T. J. Macromolecules 2002, 35, 2970.
(7) Klein, H. F.; Karsch, H. H. Inorganic Chemistry 1975, 14, 473.
(8) Kramer, J. R.; Deming, T. J. Biomacromolecules 2012, 13, 1719.
(9) Jost, R.; Brambilla, E.; Monti, J. C.; Luisi, P. L. Helvetica Chimica Acta 1980, 63, 375.
(10) Rodriguez-Hernandez, J.; Gatti, M.; Klok, H.-A. Biomacromolecules 2003, 4, 249.
(11) Morrow, J. A.; Segall, M. L.; Lund-Katz, S.; Phillips, M. C.; Knapp, M.; Rupp, B.; Weisgraber, K. H. Biochemistry 2000, 39, 11657.
(12) Houghten, R. A.; Li, C. H. Analytical Biochemistry 1979, 98, 36.

(13) Moskovitz, J.; Berlett, B. S.; Poston, J. M.; Stadtman, E. R. Proceedings of the National Academy of Sciences 1997, 94, 9585.

What is claimed is:

1. A process for preparing an amphiphilic block copolypeptide with oxidized thioether groups comprising:
    synthesizing a block copolypeptide wherein at least one of the blocks contains at least 3 consecutive hydrophobic amino acids selected from leucine, phenylalanine, alanine, isoleucine, valine, tyrosine, and tryptophan, and wherein at least one of the blocks contains at least 3 consecutive thioether containing amino acids selected from methionine, S-methyl-cysteine, S-ethyl-cysteine, S-allyl-cysteine, S-benzyl-cysteine, S-farnesyl-cysteine, S-propargyl-cysteine, S-methyl-homocysteine, S-ethyl-homocysteine, S-allyl-homocysteine, S-benzyl-homocysteine, S-farnesyl-homocysteine, and S-propargyl-homocysteine;
    adding an oxidizing reagent to the block copolypeptide; and
    reacting the block copolypeptide so that the majority of the thioether groups in the polypeptide are oxidized, thereby forming the amphiphilic block copolypeptide with oxidized thioether groups.

2. The process of claim 1, wherein the thioether containing amino acids are methionine.

3. The process of claim 1, wherein the thioether containing amino acids are one or more of S-methyl-cysteine, S-ethyl-cysteine, S-allyl-cysteine, S-benzyl-cysteine, S-farnesyl-cysteine, and S-propargyl-cysteine.

4. The process of claim 1, wherein the thioether containing amino acids are one or more of the following: S-methyl-homocysteine, S-ethyl-homocysteine, S-allyl-homocysteine, S-benzyl-homocysteine, S-farnesyl-homocysteine, and S-propargyl-homocysteine.

5. The process of claim 1, wherein the oxidized thioether groups in the amphiphilic block copolypeptide are one or more of the following: sulfoxide, and sulfone.

6. The process of claim 1 wherein the hydrophobic amino acids are one or more of L-leucine, L-phenylalanine, L-alanine, L-isoleucine, L-valine, L-tyrosine, and L-tryptophan.

7. The process of claim 1, wherein the block copolypeptide is a diblock copolypeptide.

8. The process of claim 1, wherein the block copolypeptide is a triblock copolypeptide.

9. The process of claim 1, wherein the thioether containing amino acids are L-methionine.

10. The process of claim 1, wherein the hydrophobic amino acids are L-leucine or L-phenylalanine.

11. The process of claim 1, wherein the oxidizing reagent comprises $H_2O_2$.

12. The process of claim 1, wherein the amphiphilic block copolypeptide with oxidized thioether groups is
    poly(L-methionine-sulfoxide)$_{65}$-block-poly(L-leucine$_{0.5}$-co-L-phenylalanine$_{0.5}$)$_{20}$;
    poly(Nϵ-trifluoroacetyl-L-lysine)$_{11}$-block-poly(L-methionine sulfoxide)$_{55}$-block-poly(L-leucine$_{0.5}$-co-L-phenylalanine$_{0.5}$)$_{20}$;
    poly(Nϵ-trifluoroacetyl-L-lysine)$_{21}$-block-poly(L-methionine sulfoxide)$_{55}$-block-poly(L-leucine$_{0.5}$-co-L-phenylalanine$_{0.5}$)$_{20}$;
    poly(L-lysine)$_{10}$-block-poly(L-methionine sulfoxide)$_{55}$-block-poly(L-leucine$_{0.5}$-co-L-phenylalanine$_{0.5}$)$_{20}$;
    poly(L-lysine)$_{20}$-block-poly(L-methionine sulfoxide)$_{55}$-block-poly(L-leucine$_{0.5}$-co-L-phenylalanine$_{0.5}$)$_{20}$;
    poly(L-homoarginine)$_{10}$-block-poly(L-methionine sulfoxide)$_{55}$-block-poly(L-leucine$_{0.5}$-co-L-phenylalanine$_{0.5}$)$_{20}$; or
    poly(L-homoarginine)$_{20}$-block-poly(L-methionine sulfoxide)$_{55}$-block-poly(L-leucine$_{0.5}$-co-L-phenylalanine$_{0.5}$)$_{20}$.

* * * * *